United States Patent
Yamaguchi et al.

(10) Patent No.: US 10,036,760 B2
(45) Date of Patent: Jul. 31, 2018

(54) SAMPLE ANALYZER AND SAMPLE ANALYSIS METHOD

(71) Applicant: SYSMEX CORPORATION, Kobe-shi, Hyogo (JP)

(72) Inventors: Keiichi Yamaguchi, Kobe (JP); Hiroshi Kurono, Kobe (JP); Katsushi Kobayashi, Kobe (JP)

(73) Assignee: SYSMEX CORPORATION, Kobe-shi (JP)

( * ) Notice: Subject to any disclaimer, the term of this patent is extended or adjusted under 35 U.S.C. 154(b) by 0 days.

(21) Appl. No.: 14/670,546

(22) Filed: Mar. 27, 2015

(65) Prior Publication Data

US 2015/0276769 A1    Oct. 1, 2015

(30) Foreign Application Priority Data

Mar. 28, 2014  (JP) ................................. 2014-068964

(51) Int. Cl.
*G01N 33/86* (2006.01)
*G06F 11/00* (2006.01)
*G01N 21/00* (2006.01)

(52) U.S. Cl.
CPC ............ *G01N 33/86* (2013.01); *G01N 21/00* (2013.01)

(58) Field of Classification Search
CPC ................................ G01N 33/86; G01N 21/00
See application file for complete search history.

(56) References Cited

U.S. PATENT DOCUMENTS

| | | | | |
|---|---|---|---|---|
| 5,631,165 A | * | 5/1997 | Chupp | ................. B01F 5/0453 422/63 |
| 2011/0079641 A1 | * | 4/2011 | Cantor | ................. G06F 19/366 235/375 |
| 2012/0270336 A1 | | 10/2012 | Haga | |
| 2014/0087472 A1 | | 3/2014 | Kurono et al. | |

FOREIGN PATENT DOCUMENTS

| | | |
|---|---|---|
| CN | 102656462 A | 9/2012 |
| JP | S54-107396 A | 8/1979 |
| JP | S61-235753 A | 10/1986 |
| JP | H07-120471 A | 5/1995 |
| JP | 2002-082118 A | 3/2002 |
| WO | 2011064982 A1 | 6/2011 |

OTHER PUBLICATIONS

The Chinese office action letter dated Oct. 9, 2017 in a counterpart Chinese patent application.

* cited by examiner

*Primary Examiner* — Paul S Hyun
(74) *Attorney, Agent, or Firm* — Metrolexis Law Group, PLLC

(57) ABSTRACT

A sample analyzer comprises an input to select a sample type to be measured from a plurality of platelet sample types of differing concentrations, a measurement part to obtain optical information of a sample, a processing part that calculates platelet aggregation information from the optical information, and an alarm part. The processing part determines whether the actual measured sample type differs from the inputted sample type based on the optical information from the measurement part, and actuates the alarm part accordingly.

20 Claims, 6 Drawing Sheets

SAMPLE ANALYZER AND SAMPLE ANALYSIS METHOD

CROSS REFERENCE TO RELATED APPLICATION

This application claims priority from prior Japanese Patent Application No. 2014-068964, filed on Mar. 28, 2014, entitled "ANALYTICAL APPARATUS SYSTEM, PROCESSING METHOD, AND COMPUTER PROGRAM", the entire contents of which are incorporated herein by reference.

BACKGROUND

This disclosure relates to a sample analyzer and a sample analysis method.

Platelet aggregation testing has been conventionally performed as a blood test. Platelet aggregation testing methods use platelet rich plasma (PRP) samples and platelet poor plasma (PPP) samples (see, for example, Japanese Patent Application Publication No. 2002-82118). PRP samples contain plasma components obtained by weak centrifugation of blood samples. PPP samples contain plasma components obtained by strong centrifugation of blood samples. PRP samples have relatively high platelet concentrations. PPP samples have relatively low platelet concentrations.

As disclosed in Japanese Patent Application Publication No. 2002-82118, samples with various platelet concentrations may be used for platelet aggregation testing. For example, a sample can have either low platelet concentration or high platelet concentration. In this case, an operator of an analyzer needs to be careful to correctly recognize which platelet concentration condition the sample to be tested has.

SUMMARY

In sample analyzers, a sample type to be measured from is inputted, the sample type selected from multiple sample types with different platelet concentrations. The sample analyzer includes a measurement part, a processing part, and an alarm part. The measurement part measures optical information of a sample. The processing part calculates information regarding the platelet aggregation of the sample from the optical information. The processing part determines whether there is a possibility that a type of the measured sample is different from the inputted sample type on the basis of the optical information measured by the measurement part, and actuates the alarm part according to the determination result.

In a sample analysis method, a sample type to be measured is selected from multiple sample types whose concentrations of platelets are mutually different, and the selected sample type is inputted. Optical information of a sample is measured. A calculation step is performed in which the information regarding the platelet aggregation of the sample is calculated from the optical information. Whether there is a possibility that the type of the measured sample is different from the inputted sample type is determined on the basis of the measured optical information, and an alarm part is actuated according to the determination result.

DETAILED DESCRIPTION

Embodiments are described with reference to drawings. The following embodiments are illustrative only.

(Sample Analyzer 1)

Figure 1:
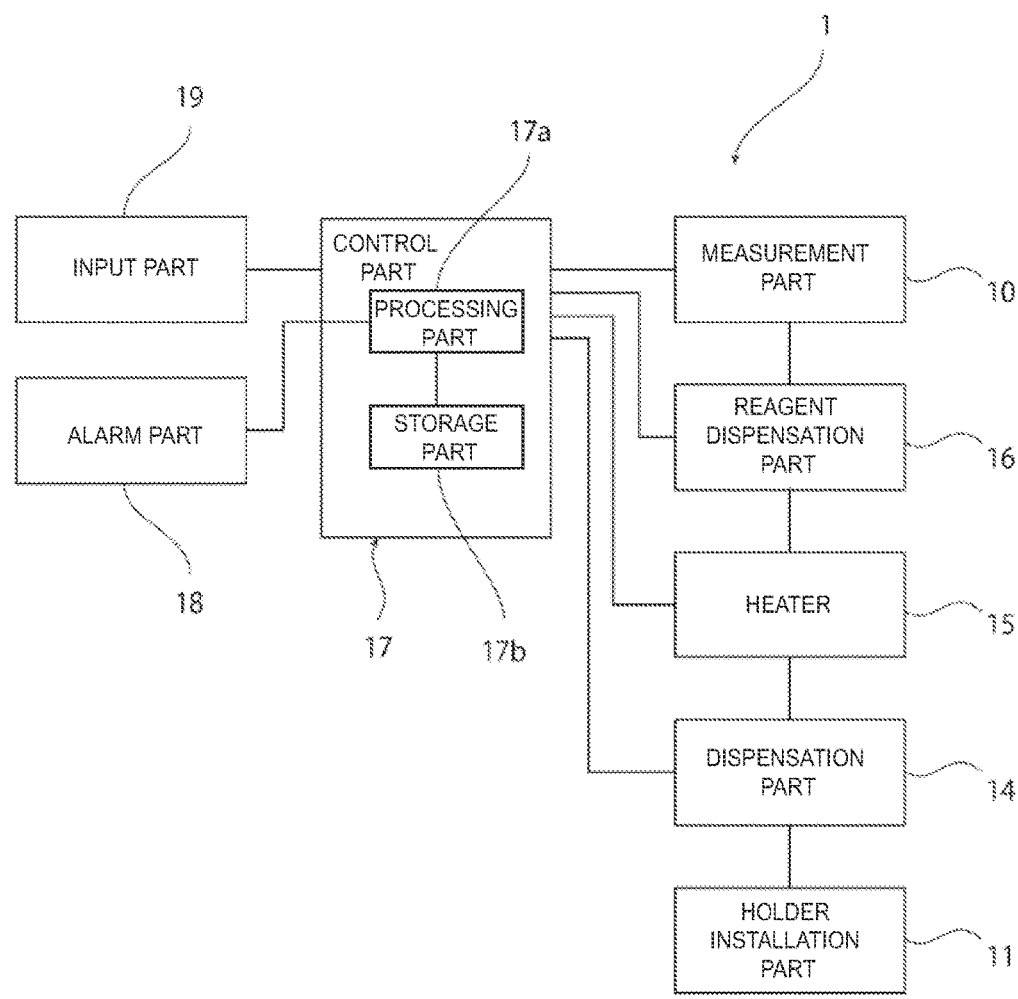
FIG. 1 is a schematic block diagram of a sample analyzer according to an embodiment.

FIG. 1 is a schematic block diagram of sample analyzer 1 according to this embodiment. Sample analyzer 1 analyzes the platelet aggregation of blood samples and outputs the information regarding the platelet aggregation of the samples. Sample analyzer 1 may be capable of analyzing other test items, such as blood coagulation and fibrinolytic capacity, in addition to the platelet aggregation, and maximum aggregation. Sample analyzer 1 may be a device capable of analyzing information regarding, for example, a maximum aggregation, an epinephrine concentration, a collagen concentration, a ristocetin concentration, and an arachidonic acid concentration. Sample analyzer 1 may be a device capable of analyzing, for example, prothrombin time (PT), activated partial thromboplastin time (APTT), fibrinogen (Fbg), extrinsic coagulation factors (II, V, VII, X), intrinsic coagulation factors (VIII, IX, XI, XII), coagulation factor XIII, thrombo test (TTO), hepaplastin test (HpT), AT III, Plg, APL, PC, FDP, D dimer, PIC, FMC, VWF:Ag, and VWF:RCo.

Samples subjected to sample analyzer 1 can be any sample containing blood platelets. In general, samples derived from blood, or blood samples are subjected to sample analyzer 1. Blood samples may be, for example, whole blood samples, or samples obtained by removing some components from whole blood samples.

Sample analyzer 1 can make measurements on multiple sample types whose concentrations of platelets mutually differ. Sample analyzer 1 may measure the optical information for the multiple sample types with the different platelet concentrations and calculate the information regarding platelet aggregation from the optical information. The sample may contain substantially no blood platelets. Specifically, at least either PRP samples or PPP samples are subjected to sample analyzer 1. An exemplary case where sample analyzer 1 makes measurements on both PRP samples and PPP samples is described here.

Sample analyzer 1 includes measurement part 10. Measurement part 10 performs various measurements on samples and reaction products in the samples. Measurement part 10 at least measures the optical information of samples containing blood platelets. Specifically, measurement part 10 measures the intensity of light transmitted through samples as optical information of the samples. In general, higher platelet concentrations of samples cause lower intensities of transmitted light, resulting in higher absorbance. Lower platelet concentrations of samples cause higher intensities of transmitted light, resulting in lower absorbance. Therefore, the measurement of the intensity of light transmitted through samples may provide the information correlated with the platelet concentration of the samples.

Measurement part 10 can employ any measurement method. Measurement part 10 is preferably configured to carry out the measurement method according to the measurement item. Specifically, measurement part 10 may include a photoemitter (not shown) and a photoreceptor (not shown) provided on the respective sides of a clear container (for example, cuvette) containing a sample or reaction products in the sample.

To measurement part 10, the sample in the container held by the holder installed in holder installation part 11 is supplied. Holder installation part 11 refers to a space in which the holder is installed.

Figure 2:
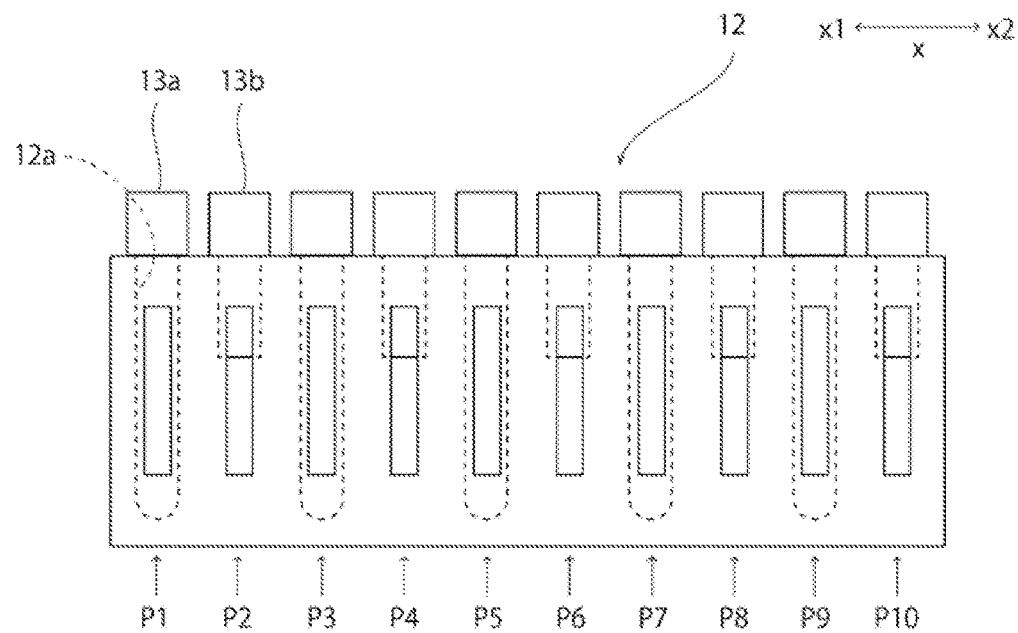
FIG. 2 is a schematic front view of a holder according to an embodiment.

FIG. 2 is a schematic front view of holder 12 according to this embodiment. Holder 12 has insertion openings 12a. Sample containers 13a and 13b are inserted to and held in insertion openings 12a. Specifically, holder 12 has multiple insertion openings 12a. Holder 12 thus can hold multiple sample containers 13a and 13b. Multiple insertion openings 12a are arranged along the x-axis direction. In the following description, the positions of insertion openings 12a from x1 side toward x2 side in the x-axis direction are referred to as positions P1 to P10, respectively.

Figure 3:
FIG. 3 is a schematic front view of one sample container 13*a* according to an embodiment.
Figure 4:
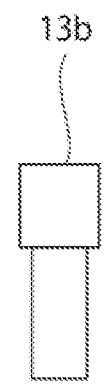
FIG. 4 is a schematic front view of another sample container 13*b* according to an embodiment.

The type of containers held by holder 12 may be the same or different. Specifically, sample containers 13a illustrated in FIG. 3 and sample containers 13b illustrated in FIG. 4 are held by holder 12. For example, sample containers 13a and sample containers 13b are alternately held by holder 12 from x1 side toward x2 side in the x-axis direction. In this case, sample containers 13a are held at odd-numbered positions P1, P3, P5, P7, and P9. Sample containers 13b are held at even-numbered positions P2, P4, P6, P8, and P10.

Sample container 13a contains a PPP sample. On the other hand, sample container 13b contains a PRP sample. Sample containers 13a and 13b have a bottomed cylindrical container body and a cap for closing the container body, respectively.

The samples in sample containers 13a and 13b held by holder 12 installed in holder installation part 11 are collected by dispensation part 14 illustrated in FIG. 1. Specifically, dispensation part 14 collects the samples in turn from multiple sample containers 13a and 13b held by holder 12. More specifically, dispensation part 14 collects the samples in turn from sample containers 13a and 13b from lower-numbered positions placed on x1 side. Dispensation part 14 supplies the collected samples to measurement part 10.

Sample analyzer 1 is configured to enable direct supply of the samples collected by dispensation part 14 to measurement part 10. Sample analyzer 1 is configured to enable supply of the samples collected by dispensation part 14 to measurement part 10 through heater 15 and reagent dispensation part 16.

Heater 15 heats the sample to a predetermined temperature for a predetermined time. Specifically, heater 15 holds the container (not shown) containing the sample dispensed by dispensation part 14 and heats the sample to a predetermined temperature for a predetermined time. The heating time and temperature can be appropriately set according to the type of sample, the type of measurement to be made, and the like.

Reagent dispensation part 16 dispenses a reagent into the sample heated by heater 15. The reagent can be appropriately selected according to the type of sample, the type of measurement to be made, and the like. The amount of reagent to be dispensed can be also appropriately determined according to the type of sample, the type of reagent, the amount of reagent, and the like. For example, a platelet aggregation inducer may be dispensed by reagent dispensation part 16 when the sample is a PPP sample. The sample into which the reagent has been dispensed by reagent dispensation part 16 is supplied to measurement part 10.

Sample analyzer 1 includes control part 17. Control part 17 controls dispensation part 14, heater 15, reagent dispensation part 16, measurement part 10, and the like. Control part 17 includes processing part 17a and storage part 17b. Processing part 17a calculates the information regarding the platelet aggregation of the sample from the optical information of the sample measured by measurement part 10. Processing part 17a performs various calculations according to analysis items. Processing part 17a also determines the possibility of incorrect recognition of the sample and controls alarm part 18 as described below in detail.

Control part 17 is connected to input part 19. Input part 19 is a part to which an operator of sample analyzer inputs various types of information. Input part 19 is configured to allow the operator to select a sample type to be measured from multiple sample types with different platelet concentrations and input the sample type. Specifically, input part 19 is configured to enable inputs of the types of samples respectively contained in multiple sample containers 13a and 13b before starting the measurements of the samples in sample containers 13a and 13b.

In this embodiment, sample analyzer 1 having input part 19 is illustrated above. It is noted that the invention is not limited to this. For example, an input part may be provided separately from a sample analyzer. For example, an input device may be provided separately from a sample analyzer and connected to the sample analyzer via the Internet line.

Control part 17 is connected to alarm part 18. Specifically, processing part 17a in control part 17 is connected to alarm part 18. Alarm part 18 gives an alarm according to the signals from processing part 17a. Alarm part 18, for example, may give an alarm to the operator through a display configured to present characters, images, or the like, or may give an alarm to the operator through sounds.

(Sample Analysis Method)

Figure 5:
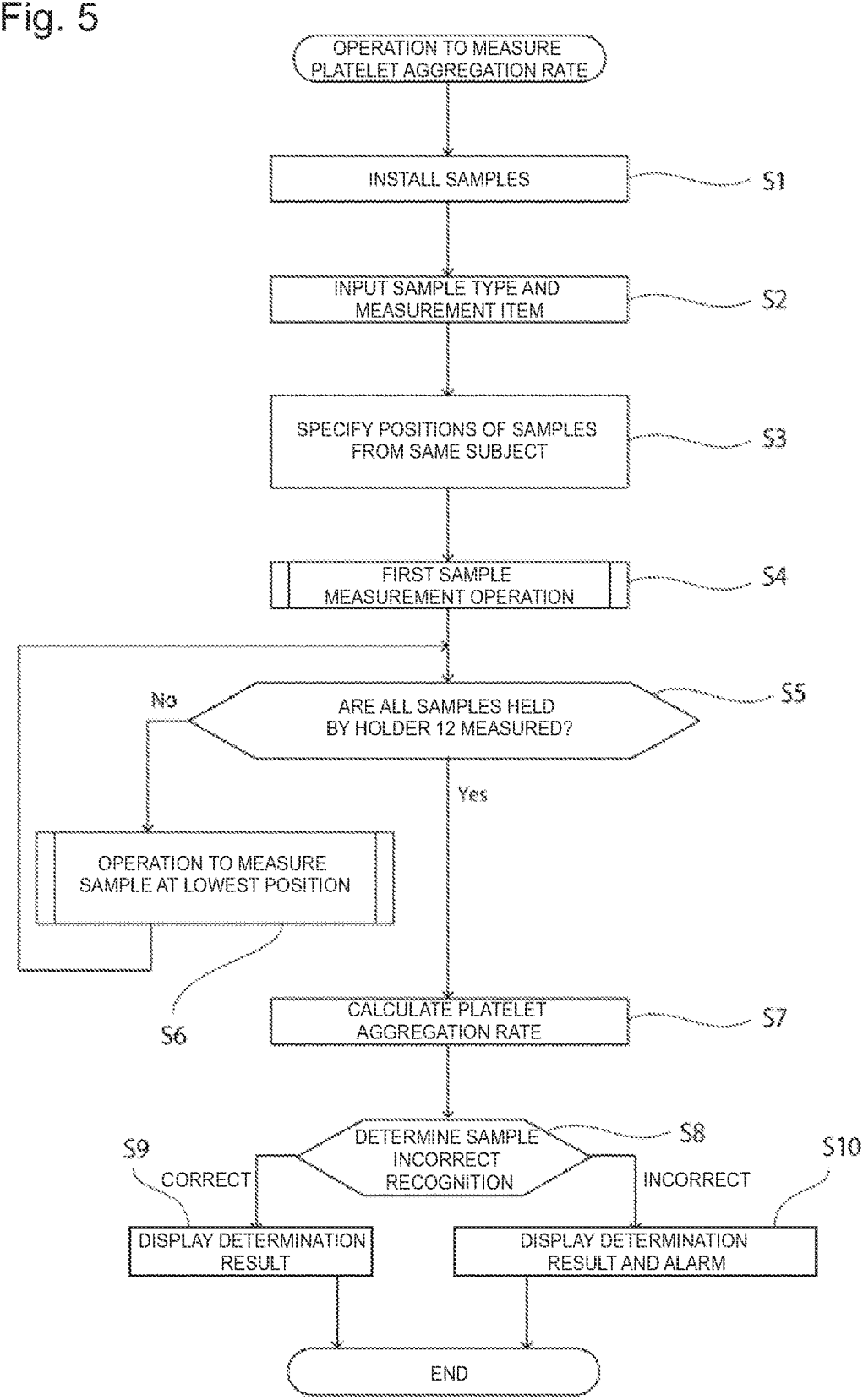
FIG. 5 is a flow chart illustrating a sample analysis procedure according to an embodiment.

FIG. 5 is a flow chart illustrating a sample analysis procedure according to this embodiment. Next, an exemplary method of analyzing a sample with sample analyzer 1 is described with reference to FIG. 5. An exemplary analysis of the maximum aggregation, the information regarding the platelet aggregation of the sample, with sample analyzer 1 is described here. In the following example, an exemplary case where the multiple sample types with different platelet concentrations include PPP and PRP samples is described.

A sample is first installed in sample analyzer 1 in step S1. Specifically, at least one sample container 13a, 13b is installed in holder 12 as illustrated in FIG. 2. Next, holder 12 having the at least one sample container 13a, 13b is installed in holder installation part 11 illustrated in FIG. 1. An exemplary arrangement is described here in which sample containers 13a containing PPP samples are installed in odd-numbered positions P1, P3, P5, P7, and P9 respectively and sample containers 13b containing PRP samples are installed in even-numbered positions P2, P4, P6, P8, and P10 respectively. The sample contained in sample container 13a placed at odd-numbered position Pn (where n is 1, 3, 5, 7, or 9) and the sample contained in sample container 13b placed at the next position, i.e., even-numbered position P(n+1) are prepared from a whole blood sample collected from the same subject.

Next, the operator of sample analyzer 1 inputs the sample type in step S2. Specifically, storage part 17b stores multiple sample types with different platelet concentrations, and the operator selects the sample type to be measured from the multiple sample types and inputs the sample type. More specifically, the operator selects and inputs the sample type to be measured for the samples contained in sample containers 13a and 13b installed in positions P1 to P10 respectively. The operator may input the sample type to be measured in order of measurement for the samples contained in sample containers 13a and 13b installed in positions P1 to P10 respectively. In the example described here, for example, the information that the sample is a PPP sample is inputted for position P1, and the information that the sample is a PRP sample is inputted for position P2.

In step S2, the information on which subject the sample is collected from is also inputted for the samples contained in sample containers 13a and 13b held at positions P1 to P10 respectively. Specifically, for example, the information that the samples are from the same subject is inputted for position P1 and position P2.

For example, when storage part 17b is caused to store the information that PPP samples are set at the odd-numbered positions and PRP samples are set at the even-numbered positions, a standardized test can be carried out in which the PPP samples are set at the odd-numbered positions and the PRP samples are set at the even-numbered positions. In this case, step S2 does not always require inputting the sample type.

In the following description, the samples contained in sample containers 13a and 13b held at position Pm (where m is an integer of 1 to 10) is referred to as an "m-th sample". For example, the sample contained in sample container 13a held at position P1 is referred to as a first sample.

In step S2, the operator inputs at least one measurement item. Specifically, the operator inputs the type of measurement for each of first to tenth samples. Examples of the measurement items include measurement items related to platelet aggregation (platelet aggregation items) and measurement items related to blood coagulation and fibrinolytic function (blood coagulation items). In this example, the operator selects measurement items including at least one platelet aggregation item for each sample in order to analyze the maximum aggregation.

Next, in step S3, processing part 17a specifies the positions of samples from the same subject on the basis of the information inputted in step S1. In this case, processing part 17a, for example, specified position P1 and position P2 as being positions of samples from the same subject. When there are no positions of samples from the same subject, processing part 17a determines that there are no positions of samples from the same subject in step S3.

Figure 6:
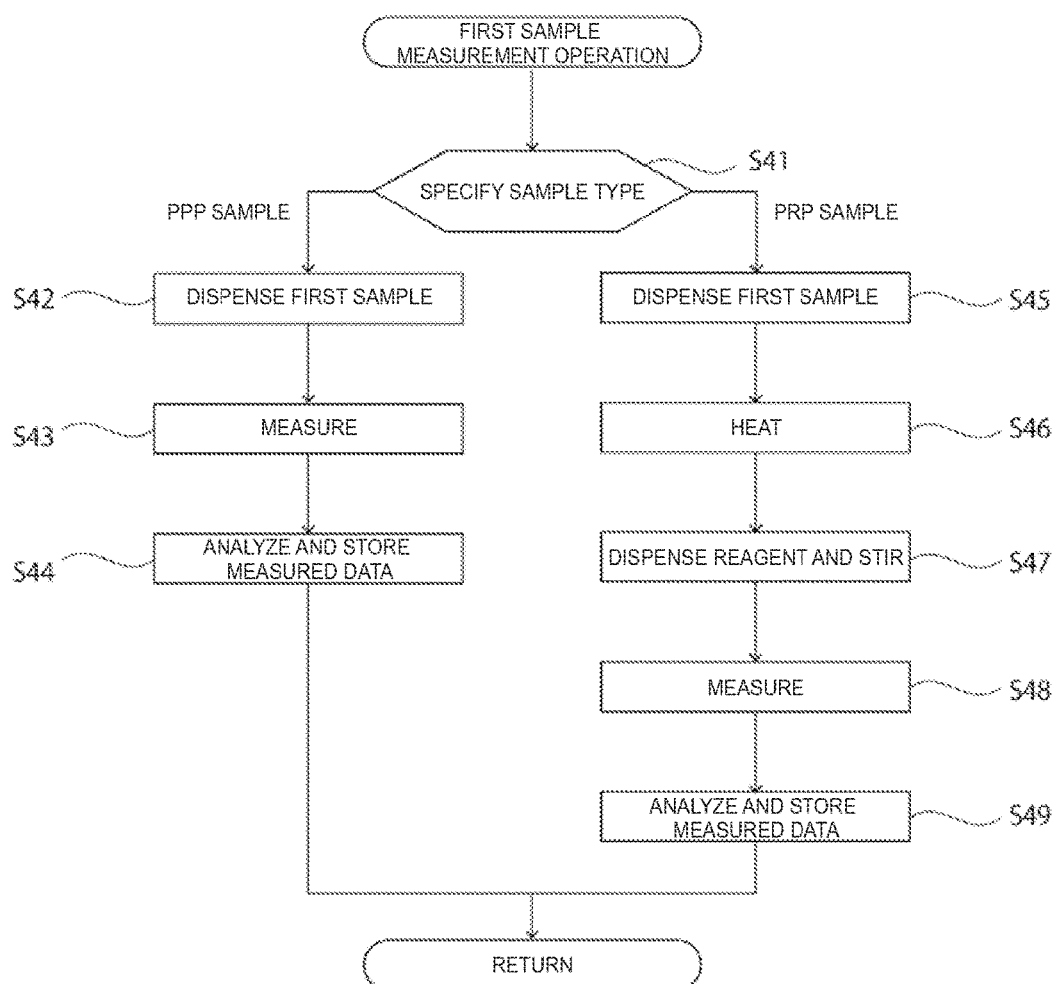
FIG. 6 is a flow chart illustrating a first sample measurement procedure according to an embodiment.

Next, in step S4, measurement operation is performed on the first sample. FIG. 6 is a flow chart illustrating a first sample measurement procedure according to this embodiment. In step S4 of the first sample measurement operation, as illustrated in FIG. 6, processing part 17a first specifies the sample type inputted for the first sample in step S41. As in this example, when the first sample is specified as a PPP sample on the basis of the input information in step S41, the process goes to step S42. When the first sample is specified as a PRP sample on the basis of the input information in step S41, the process goes to step S45.

When the first sample is specified as a PPP sample, processing part 17a first causes dispensation part 14 to dispense the first sample into measurement part 10 in step S42. Specifically, processing part 17a causes dispensation part 14 to dispense the first sample into measurement containers and move the measurement containers to measurement part 10.

Next, processing part 17a causes measurement part 10 to measure the optical information of the supplied first sample in step S43. Specifically, processing part 17a causes measurement part 10 to measure the intensity of light transmitted through the first sample over the predetermined period as the optical information of the first sample. The measured intensity of light transmitted through the first sample is outputted to processing part 17a.

Next, processing part 17a analyzes the outputted measurement data and causes storage part 17b to store the analysis results and inspection results regarding the absorbance and others in step S44.

When the first sample is specified as a PRP sample, processing part 17a first causes dispensation part 14 to dispense the first sample in step S45. Specifically, processing part 17a causes dispensation part 14 to dispense the first sample into the measurement containers. Processing part 17a causes dispensation part 14 to supply the measurement containers containing the dispensed first sample to heater 15.

Next, processing part 17a causes heater 15 to heat the measurement containers containing the dispensed first sample at a predetermined temperature for a predetermined period in step S46.

Next, processing part 17a causes reagent dispensation part 16 to supply the reagent corresponding to the measurement item to the measurement containers and stir the reagent and the first sample in step S47. Processing part 17a here causes reagent dispensation part 16 to supply a platelet aggregation inducer to the measurement containers. Subsequently, processing part 17a causes a movement mechanism (not shown) to move the measurement containers to measurement part 10.

Next, processing part 17a causes measurement part 10 to measure the optical information of the reaction products in the first sample in step S48. Specifically, processing part 17a causes measurement part 10 to measure the intensity of light transmitted through the first sample over a predetermined period as the optical information of the first sample. The measured intensity of light transmitted through the first sample is outputted to processing part 17a.

Next, processing part 17a analyzes the outputted measurement data and causes storage part 17b to store the analysis results and inspection results regarding the absorbance and others in step S49.

Figure 7:
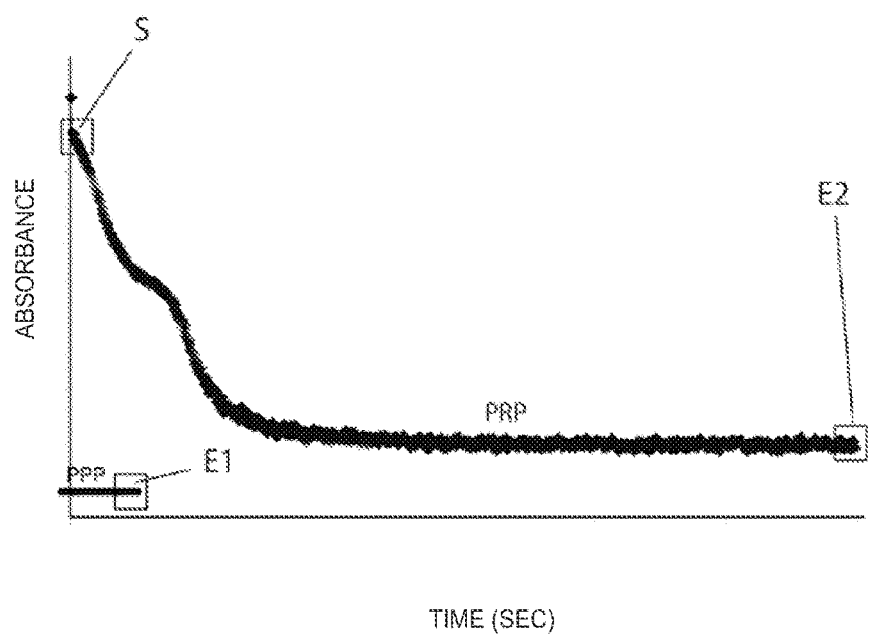
FIG. 7 is an exemplary graph illustrating the absorbance of PPP and PRP samples.

FIG. 7 is an exemplary graph illustrating the absorbance of the PPP and PRP samples. As illustrated in FIG. 7, the absorbance of the PPP sample is substantially constant because there is no reaction in the PPP sample. On the other hand, the platelet aggregation inducer is supplied to the PRP sample. This addition of the platelet aggregation inducer initiates aggregation of blood platelets in the PRP sample. The absorbance of the PRP sample accordingly decreases with time after reagent addition.

As illustrated in FIG. 5, after completion of the first sample measurement operation in step S4, processing part 17a determines whether all the samples held by holder 12 are measured (step S5). When processing part 17a determines that all the samples held by holder 12 are not measured in step S5, the process goes to step S6.

In step S6, the measurement operation is performed on the sample at the lowest position among unmeasured samples. The measurement operation in step S6 is substantially the same as the first sample measurement operation in step S4. Therefore, the description regarding the first sample measurement operation in step S4 is incorporated by reference for the measurement operation in step S6.

After completion of the measurement operation in step S6, the process returns to step S5. In step S5, processing part 17a determines again whether all the samples held by holder 12 are measured. Step S5 and step S6 accordingly repeat until the measurement is complete for all the samples.

When processing part 17a determines that all the samples held by holder 12 are measured in step S5, the process next goes to step S7.

In Step 7, processing part 17a calculates the information regarding the platelet aggregation of the sample from the measured optical information and causes storage part 17b to store the calculated results. Specifically, processing part 17a first specifies the positions of samples from the same subject on the basis of the information inputted in step S1. In this case, for example, the first sample (PPP sample) placed in sample container 13a held at position P1 and the second sample (PRP sample) placed in sample container 13b held at position P2 are samples from the same subject. Processing part 17a thus specifies position P1 and position P2 as being positions of samples from the same subject.

Next, processing part 17a reads from storage part 17b the absorbance data of the PPP sample and PRP data wherein these PPP and PRP samples are from the same subject. Next, processing part 17a specifies the absorbance of the PPP sample at measurement end E1 (see FIG. 7), the absorbance of the PPP sample just after dispensing the reagent into the PRP sample, and the absorbance of the PRP sample at measurement end E2, from the read absorbance data. When the measurement of absorbance is started just after dispensing the reagent into the PRP sample here, the absorbance of the PRP sample just after dispensing the reagent into the PRP sample is the absorbance at measurement start time S. When the measurement of absorbance is not started just after dispensing the reagent into the PRP sample, the absorbance of the PRP sample just after dispensing the reagent into the PRP sample may be estimated from the measured absorbance.

The absorbance of the PPP sample substantially remains the same over the measurement period as mentioned above. Therefore, the absorbance of the PPP sample at measurement end E1 may be replaced by, for example, the absorbance of the PPP sample in the middle of the absorbance measurement.

The absorbance of the PRP sample at measurement end E2 is the absorbance of the PRP sample after the reaction of the PRP sample is substantially completed.

Next, processing part 17a calculates the maximum aggregation (%) according to equation (1) below. Processing part 17a causes storage part 17b to store the calculated maximum aggregation.

$$\text{AGGREGATION (\%)} = ((PRP\_s - PRP\_e)/(PRP\_s - PPP)) \times 100 \quad (1)$$

In equation (1), AGGREGATION is the maximum aggregation (%), PRP_s is the absorbance of the PRP sample just after dispensing the reagent into the PRP sample, PRP_e is the absorbance of the PRP sample at measurement end E2, and PPP is the absorbance of the PPP sample at measurement end E1.

Next, processing part 17a determines whether the sample is incorrectly recognized in step S8. Specifically, processing part 17a determines whether there is a possibility that the type of the measured sample is different from the sample type inputted in step S2 on the basis of the optical information measured by measurement part 10. Specifically, processing part 17a determines whether the sample type is the same or different on the basis of the information used for calculating the information regarding the platelet aggregation of the sample among the optical information. More specifically, processing part 17a determines whether the sample type is the same or different on the basis of the absorbance of the sample, more specifically PRP_s or PPP. Specifically, storage part 17b stores an optical condition set to define a range of optical information for each of the sample types. Specifically, storage part 17b stores a PPP sample absorbance condition as the optical condition for the PPP sample. Storage part 17b stores a PRP sample absorbance condition as the optical condition for the PRP sample. As mentioned above, the absorbance of the PPP sample is relatively low and the absorbance of the PRP sample is relatively high. Therefore, the absorbance range set as the PPP sample absorbance condition is lower than the absorbance range set as the PRP sample absorbance condition. Processing part 17a reads the optical condition for the inputted sample type from storage part 17b. Processing part 17a determines whether the optical information of the measured sample meets the read optical condition. When processing part 17a determines that the optical information of the measured sample fails to meet the read optical condition, it is determined that there is a possibility that the type of the sample is different from the inputted sample type.

For example, the information that the sample is a PPP sample is inputted for first position P1 in step S2. Processing part 17a accordingly reads the PPP sample absorbance condition from storage part 17b. Processing part 17a next determines whether the measured PPP meets the optical condition for the PPP sample. For example, when the PRP sample is incorrectly held at first position P1, the absorbance measured as PPP fails to meet the PPP sample absorbance condition. The absorbance measured as PPP is higher than the absorbance range set as the PRP sample absorbance condition. In this case, processing part 17a determines that there is a possibility that the type of the sample placed at first position P1 is different from the sample type (PPP sample) inputted in step S2.

For example, the information that the sample is a PRP sample is inputted for second position P2 in step S2. Processing part 17a accordingly reads the PRP sample absorbance condition from storage part 17b. Processing part 17a next determines whether the measured PRP_s meets the optical condition for the PRP sample. For example, when the PPP sample is incorrectly held at second position P2, the absorbance measured as PRP_s fails to meet the PRP sample absorbance condition. The absorbance measured as PRP_s is lower than the absorbance range set as the PRP sample absorbance condition. In this case, processing part 17a determines that there is a possibility that the type of the sample placed at second position P2 is different from the sample type (PRP sample) inputted in step S2.

In this embodiment, the calculation of the maximum aggregation in step S7 followed by the determination of sample incorrect recognition in step S8 is illustrated above. It is noted that the invention is not limited to this. For example, step S7 and step S8 may be performed at the same time, or step S7 may be performed after step S8.

When processing part 17a does not determine that the type of the measured sample is different from the sample type inputted in step S2 (processing part 17a determines that these sample types are in agreement with each other) in step S8, the process goes to step S9. In step S9, processing part 17a causes a display part to present the results, such as the calculated maximum aggregation. For example, when alarm part 18 includes the display part, processing part 17a causes the display part in alarm part 18 to present the results, such as the calculated maximum aggregation. When alarm part 18 has no display part, a display part may be provided separately.

When, in step S8, processing part 17a determines that the type of the measured sample is different from the sample type inputted in step S2, the process goes to step S10. In step S10, processing part 17a causes the display part to present the results, such as the calculated maximum aggregation. Processing part 17a actuates alarm part 18. Specifically, processing part 17a causes alarm part 18 to give an alarm of the information indicating an error in the sample type in step S10. This information indicating an error in the sample type includes pieces of information indicating the incorrect position of the sample type in holder 12 and pieces of information indicating the incorrect input of the sample type in step S2.

For example, when alarm part 18 includes the display part, processing part 17a causes alarm part 18 to present the information indicating an error in the sample type. For example, processing part 17a may cause alarm part 18 to present character information, figures, or the like indicating an error in the sample type. For example, when alarm part 18 includes the display part configured to present the inspection results, processing part 17a may cause alarm part 18 to hide the analysis results, such as the maximum aggregation calculated for the samples determined to possibly have errors in the sample type. For this case, processing part 17a may be configured to cause alarm part 18 to mask some measurement results to be hidden or to display different colors from those in other parts.

When alarm part 18 includes the display part, processing part 17a may cause alarm part 18 to present the reason why the sample type is possibly incorrect, together with the information indicating an error in the sample type. For example, processing part 17a may cause alarm part 18 to present the information that the inputted sample type is a PPP sample but the measured absorbance is over the absorbance range set as the PPP sample absorbance condition, together with the information indicating an error in the sample type.

For example, when alarm part 18 include a sound part configured to release sounds, processing part 17a may cause alarm part 18 to make sounds or words indicating an error in the sample type. For example, when alarm part 18 is a light-emitting display or the like, processing part 17a may cause alarm part 18 to emit light indicating an error in the sample type. Alarm part 18 may include two or more parts selected from a display part, sound part, light-emission part, or the like.

In sample analyzer 1, as described above, processing part 17a determines whether there is a possibility that the type of the measured sample is different from the inputted sample type on the basis of the optical information measured by measurement part 10, and actuates the alarm part 18 according to the determination result. The operator of sample analyzer 1 accordingly knows possibilities of, for example, sample installation mistake and sample-type input mistake. The operator can accordingly check the position of the sample installed and the input information on the sample type again. In other words, even when an incorrect recognition of a sample occurs due to sample installation mistake, sample-type input mistake, or the like, sample analyzer 1 makes the operator less likely to overlook the incorrect recognition of the samples.

In sample analyzer 1, processing part 17a determines whether the type of the measured sample is different from the inputted sample type on the basis of the information used for calculating the information regarding the platelet aggregation of the sample among the optical information. That is, processing part 17a determines whether the sample is incorrectly recognized on the basis of the data used for actual analysis. Therefore, a special measurement is not always required separately for determining whether the sample is incorrectly recognized. Sample analyzer 1 thus can analyze the sample accurately and quickly.

(Other Embodiments)

In the analysis of multiple samples, if processing part 17a determines that the sample types of two or more sample containers 13a and 13b are possibly different from the inputted sample types, processing part 17a may cause alarm part 18 to give an alarm indicating a possibility that sample containers 13a and 13b determined as possibly different in the sample type may be held in wrong positions in holder 12. When the optical information of the sample contained in one of the two or more sample containers each determined as having the different sample type meets the optical condition set for the sample type inputted for a different one of the sample containers, and the optical information of the sample contained in the different sample container meets the optical conditions set for the sample type inputted for the one sample container, processing part 17a may cause alarm part 18 to give an alarm indicating a possibility that the holding position of the one sample container and the holding position of the other container may be wrong.

For example, it is assumed that sample container 13b containing a PRP sample is incorrectly placed at first position P1 and sample container 13a containing a PPP sample is incorrectly placed at second position P2. In this case, the platelet concentration of the PRP sample contained in sample container 13b placed at first position P1 is higher than the optical condition set for the PPP sample being the sample type inputted for first position P1. The platelet concentration of the PRP sample contained in sample container 13b placed at first position P1 meets the optical condition set for the PRP sample being the sample type inputted for second position P2. The platelet concentration of the PPP sample contained in sample container 13a placed at second position P2 is lower than the optical condition set for the PRP sample being the sample type inputted for second positions P2. The platelet concentration of the PPP sample contained in sample container 13a placed at second position P2 meets the optical condition set for the PPP sample being the sample type inputted for first position P1. For such a case, processing part 17a may be configured to cause alarm part 18 to give an alarm indicating a possibility that the sample container placed at first position P1 and the sample container placed at second position P2 may be held in wrong positions, or may exchange their positions, for example. In this case, the operator of sample analyzer 1 can know a possibility of an installation mistake of sample containers 13a and 13b.

In the analysis of multiple samples having different platelet concentrations and collected from the same subject, processing part 17a may actuate alarm part 18 only when determining that the sample is incorrectly recognized for the sample for which the information of relatively high platelet concentration is inputted. For example, the absorbance of the sample with a low platelet concentration may become high when it is a chylous sample. For this reason, the sample may not be incorrectly recognized even if the sample is determined to be incorrectly recognized for the sample for which the information of relatively low platelet concentration is inputted. When the measured absorbance of a sample with a relatively high platelet concentration, e.g., a PRP sample is below the absorbance range set as the optical condition for PRP samples, there is a high probability that the sample is incorrectly recognized. Therefore, processing part 17a may be configured to actuate alarm part 18 only when determining that the sample is incorrectly recognized for the samples with a relatively high platelet concentration.

Processing part 17a may be configured to determine that the type of a sample is different from the inputted sample type every time the measurement of one sample is completed. In this case, processing part 17a may be configured to actuate alarm part 18 just after determining that there is a possibility of incorrect recognition of the sample type. Processing part 17a may be configured to cause measurement part 10 to stop the subsequent measurement when determining that there is a possibility of incorrect recognition of the sample type. In such cases, the operator of sample analyzer 1 can know a possibility of incorrect recognition of the sample in early time.

Measurement part 10 may be configured to measure multiple types of information regarding blood platelets. In this case, processing part 17a may be configured to make an incorrect recognition determination using information that is different from the optical information and used for calculating the information regarding the platelet aggregation of samples.

In this way, embodiments described above provide a sample analyzer that makes an operator less likely to overlook incorrect recognition of a sample when the incorrect recognition of the sample occurs.

The invention includes other embodiments in addition to the above-described embodiments without departing from the spirit of the invention. The embodiments are to be considered in all respects as illustrative, and not restrictive. The scope of the invention is indicated by the appended claims rather than by the foregoing description. Hence, all configurations including the meaning and range within equivalent arrangements of the claims are intended to be embraced in the invention.

The invention claimed is:

1. A sample analyzer comprising:
a memory in which sample type information relevant to a sample to be measured is stored, wherein the sample type information comprises: a first range of platelet aggregation values for a platelet rich plasma (PRP) sample type; and a second range of platelet aggregation values for a platelet poor plasma (PPP) sample type;
a user interface that receives a selection of a sample type among one of the PRP sample type and the PPP sample type for the sample;
a measurement part comprising a photoemitter and a photoreceptor, wherein the measurement part measures optical information of the sample;
a display; and,
a controller that is configured with program instructions to perform operations comprising:
comparing actual platelet aggregation information of the sample based on the measured optical information of the sample with one of: the first range of platelet aggregation values for the PRP sample type; and the second range of platelet aggregation values for the PPP sample type corresponding to the received sample type selection of the sample to determine whether a difference exists between the one of: the first range of platelet aggregation values; and the second range of platelet aggregation values for the received selection of the sample type, and the actual platelet aggregation information of the sample based on the comparison; and
controlling the display to display a result of the comparison between the one of: the first range of platelet aggregation values; and the second range of platelet aggregation values for the received selection of the sample type and the actual platelet aggregation information of the selected sample.

2. The sample analyzer according to claim 1, wherein,
the controller is configured with the program instructions to perform operations further comprising controlling the display to display to information indicating an error in the sample type selection for the sample when the actual platelet aggregation information of the sample based on the measured optical information of the sample is different from the received sample type selection of the sample based on the comparison.

3. The sample analyzer according to claim 1, wherein
the measurement part obtains optical information of the sample prepared in a manner based on the selected one of: the PRP sample type and the PPP sample type, and
the controller is configured with the program instructions to perform operations further comprising calculating the actual platelet aggregation information of the sample based on the obtained optical information of the sample and the selected one of: the PRP sample type and the PPP sample type.

4. The sample analyzer according to claim 1, further comprising a reagent dispenser that dispenses a reagent to the sample according to the sample type information stored in the memory when the received selection indicates that the PPP sample type selection has been received for the sample, wherein
the measurement part measures the optical information of the sample just after the reagent dispenser dispenses the reagent, and
the controller is configured with the program instructions to perform operations further comprising
comparing the actual platelet aggregation information of the sample with the second range of platelet aggregation values for the PPP sample type to determine whether a difference exists between the actual platelet aggregation information of the sample and the second range of platelet aggregation values for the PPP sample type, and
controlling the display to display a result of the comparing.

5. The sample analyzer according to claim 1, wherein:
the selected sample type of the sample comprises the PRP sample type;
the measurement part measures the optical information of the sample during a measurement period; and
the controller is configured with the program instructions to perform operations further comprising
comparing the actual platelet aggregation information of the sample with the first range of platelet aggregation values for the PRP sample type to determine whether a difference exists between the actual platelet aggregation information of the sample and the first range of platelet aggregation values for the PRP sample type, and
controlling the display to display the result of the comparison, based on the optical information obtained at an end of the measurement period.

6. The sample analyzer according to claim 1, wherein
the sample type information stored in the memory further comprises: a first optical condition for the PRP sample type and a second optical condition for the PPP sample type, and
the controller is configured with the program instructions to perform operations further comprising:
reading one of the stored first optical condition or the stored second optical condition for the PRP or PPP sample type from the memory corresponding to the selected sample type for the sample,
determining whether the optical information of the measured sample meets the read first or second optical condition, and
controlling the display based on a result of determining whether the optical information of the measured sample meets the read first or second optical condition.

7. The sample analyzer according to claim 6, further comprising a sample container holder, wherein:
the memory stores the received selection of the sample type according to a respective position of the sample in the sample container holder, the respective position of the sample corresponding to the selected sample type for the sample;
the sample is contained in a sample container held in the sample container holder;
the sample container holding the sample is placed in the respective position in the sample container holder before the measurement part starts a measurement of the sample; and
the measurement part measures the sample in the sample container in turn according to the respective position of the sample in the sample container held in the sample container holder.

8. The sample analyzer according to claim 7, wherein the controller is configured with the program instructions to perform operations further comprising:
determining an actual sample type of the sample based on the comparing actual platelet aggregation information of the sample based on the measured optical information of the sample with one of: the first range of platelet aggregation values for the PRP sample type; and the second range of platelet aggregation values for the PPP sample type based on the received selection; and
controlling the display to present an alarm upon determining that the actual sample type of the sample from the sample container is different from the received selection of the sample type.

9. The sample analyzer according to claim 1, wherein the controller is configured with the program instructions to perform operations further comprising:
determining an actual sample type of the sample based on the comparing actual platelet aggregation information of the sample based on the measured optical information of the sample with one of: the first range of platelet aggregation values for the PRP sample type; and the second range of platelet aggregation values for the PPP sample type based on the received selection; and
stopping the measurement part from performing a subsequent measurement when it is determined based on the comparing, that the actual sample type of the sample differs from the selected sample type.

10. A method of analyzing a sample to be measured, comprising:
storing sample type information relevant to the sample in a memory, wherein the sample type information comprises a first range of platelet aggregation values for a platelet rich plasma (PRP) sample type; and a second range of platelet aggregation values for a platelet poor plasma (PPP) sample type;
receiving a selection of a sample type among one of the PRP sample type and the PPP sample type for the sample;
measuring optical information of the sample with an optical measurement part;
comparing, in a controller, actual platelet aggregation information of the sample based on the measured optical information of the sample with one of: the first range of platelet aggregation values; and the second range of platelet aggregation values of the stored sample type information corresponding to the received selection of the sample type of the sample to determine whether a sample type associated with the measured optical information is different from the selected sample type; and
displaying, on a display, an alarm according to a result of the comparison.

11. The method of analyzing a sample according to claim 10, wherein displaying, on the display, the alarm according to the result of the comparison further comprises:
determining, in the controller, a possibility that the sample type associated with the measured optical information is different from the selected sample type based on the comparing, in the controller, the actual platelet aggregation information of the sample with the one of: the first range of platelet aggregation values; and the second range of platelet aggregation values of the stored sample type information corresponding to the received selection of the sample type of the sample, and determining that the sample type associated with the measured optical information is different from the selected sample type; and
displaying, on the display, as the alarm according to the result of the comparison, the possibility that the sample type associated with the measured optical information is different from the selected sample type.

12. The method of analyzing a sample according to claim 10, wherein
measuring the optical information of the sample with the optical measurement part comprises obtaining optical information of the sample prepared in a manner based on the selected one of: the PRP sample type and the PPP sample type; and
calculating, in the controller, the actual platelet aggregation information of the sample based on the obtained optical information of the sample and the selected one of: the PRP sample type and the PPP sample type.

13. The method of analyzing a sample according to claim 10, further comprising dispensing, using a reagent dispenser, a reagent into the sample, wherein:
measuring the optical information of the sample with an optical measurement part comprises measuring at least the optical information of the sample just after dispensing, using the reagent dispenser, the reagent into the sample; and
comparing, in the controller, actual platelet aggregation information of the sample based on the measured optical information of the sample with one of the first range of platelet aggregation values and second range of platelet aggregation values of the stored sample type information corresponding to the received selection of the sample type of the sample to determine whether the sample type associated with the measured optical information is different from the selected sample type comprises performing the comparing, in the controller, based on the measuring at least the optical information of the sample just after dispensing, using the reagent dispenser, the reagent into the sample.

14. The method of analyzing a sample according to claim 10, wherein
measuring optical information of the sample with an optical measurement part comprises measuring optical information of the sample with an optical measurement part during a measurement period, and
displaying, on the display, the alarm according to the result of the comparison comprises displaying, on the display, the alarm according to the result of the comparison based on at least the optical information measured at an end of the measurement period.

15. The method of analyzing a sample according to claim 10, wherein the sample type information stored in the memory further comprises a first optical condition that defines a first optical information range for the PRP sample type and a second optical condition that defines a second optical information range for the PPP sample type, the method further comprising:
reading one of the stored first optical condition or the stored second optical condition for the PRP or PPP sample type from the memory corresponding to the selected sample type for the sample; and
comprises comparing, in the controller, the measured optical information of the sample and the read one of the stored first optical condition or the stored second optical condition corresponding to the selected sample type of the sample to determine whether the optical information of the measured sample corresponds to the selected sample type of the sample.

16. The method of analyzing a sample according to claim 10, further comprising:
placing a plurality of samples to be analyzed in a sample container holder;
storing a sample type of each the plurality of samples designated according to a respective position of each of the plurality of samples in sample containers held in the sample container holder; and
measuring each of the plurality of samples in the sample containers held in the sample container holder in turn according to the respective position of each of the plurality of samples in the sample containers held in the sample container holder.

17. The method of analyzing a sample according to claim 16, wherein the comparing further comprises comparing, in the controller, actual platelet aggregation information of two or more of the samples in the sample containers held in the sample container holder with one of the first range of platelet aggregation values and second range of platelet aggregation values of the stored sample type information based on the sample type designated according to the respective position of each of the two or more samples to determine whether the sample type designated according to the respective position of each of the two or more samples is in error and displaying an alarm indicating a possibility that the two or more samples in the sample containers are held in wrong positions in the sample container holder.

18. A sample analyzer comprising:
a holder having openings into which at least a first sample container and a second sample container are to be inserted and held, the first sample container containing a first sample and held in a first position corresponding to a Platelet Rich Plasma (PRP) sample type, and the second sample container containing a second sample and held in a second position corresponding to a Platelet Poor Plasma (PPP) sample type;
a measurement part comprising a photoemitter and a photoreceptor, wherein the measurement part obtains optical information of one of the first sample and the second sample;
a memory in which sample type information relevant to the first sample and the second sample is stored, wherein the sample type information comprises a first range of platelet aggregation values for the PRP sample type and a second range of platelet aggregation values for the PPP sample type;
a display; and
a controller that is configured with program instructions to perform operations comprising:
calculating information about a platelet aggregation activity of the measured one of the first sample and the second sample based on the obtained optical information,
determining whether the calculated platelet aggregation activity of the measured one of the first sample and the second sample based on the obtained optical information is outside one of the first range of platelet aggregation values for the PRP sample type and the second range of platelet aggregation values for the PPP sample type corresponding to the first position or the second position in which the measured one of the first sample and the second sample is held, and
displaying an alarm in a condition in which the calculated platelet aggregation activity of the measured one of the first sample and the second sample is determined to be outside one of the first range of platelet aggregation values for the PRP sample type and the second range of platelet aggregation values for the PPP sample type corresponding to the first position or the second position in which the measured one of the first sample and the second sample is held.

19. A sample analyzer comprising:
a memory in which sample type information relevant to a sample to be measured is stored, wherein the sample type information comprises a first range of platelet aggregation values for a platelet rich plasma (PRP) sample type and a second range of platelet aggregation values for a platelet poor plasma (PPP) sample type;
a sample holder comprising a plurality of sample holding positions, first ones of the plurality of holding positions designated to hold samples of the PRP sample type and second ones of the plurality of holding positions designated to hold samples of the PPP sample type, a position of the sample in one of the first ones of the plurality of holding positions or the second ones of the plurality of holding positions based on a sample type of the sample establishing a presumptive sample type among the PRP sample type and the PRP sample type;
a measurement part comprising a photoemitter and a photoreceptor, the measurement part measuring optical information of the sample;
a display; and,
a controller that is configured with program instructions to perform operations comprising:
calculating an actual platelet aggregation information of the sample based on the measured optical information of the sample;
comparing the actual platelet aggregation information of the sample calculated based on the measured optical information of the sample with one of the first range of platelet aggregation values for the PPP sample type and the second range of platelet aggregation values for the PRP sample type corresponding to the presumptive sample type for the sample to determine whether a difference exists between the one of the first range of platelet aggregation values and the second range of platelet aggregation values for the presumptive sample type and the actual platelet aggregation information of the sample; and controlling the display to display a result of the comparison.

20. A method of analyzing a blood sample, the method comprising:

receiving, into a sample analyzer, an information input identifying a sample type of a sample to be measured as either a platelet rich plasma (PRP) sample type sample type or a platelet poor plasma (PPP) sample type;

measuring, by the sample analyzer, optical information of the sample to determine an actual sample type of the sample, wherein the optical information of the sample corresponds to an actual platelet aggregation information of the sample;

comparing, by the sample analyzer, the actual sample type based on the measured optical information with the information input identifying the sample type;

determining, by the sample analyzer, whether the actual sample type based on the measured optical information and the inputted sample type information are different; and displaying, by the sample analyzer, a result of the comparison.

* * * * *